United States Patent [19]

Babaian et al.

[11] Patent Number: 4,713,239

[45] Date of Patent: Dec. 15, 1987

[54] ANTIANGINAL FILM AND METHOD OF TREATING ISCHEMIC HEART DISEASE

[75] Inventors: Eduard A. Babaian; Galina A. Gerasimova; Anatoly B. Davydov; Rustam I. Utyamyshev; Gennady L. Khromov; Vladimir I. Metelitsa; Anatoly M. Vikhert; Konstantin L. Savvateev; Vladimir K. Piotrovsky; Elizaveta B. Novikova, all of Moscow, U.S.S.R.

[73] Assignees: Vsesojuny Kardiologichesky Nauchny Tsentr Adkaemii Meditsinski Nauk SSSR; Vsesojuzny Nauchno-Issledovatelsky I Ispytateiny Institut Meditsinskoi Tekhniki, both of Moscow, U.S.S.R.

[21] Appl. No.: 799,210

[22] Filed: Nov. 19, 1985

Related U.S. Application Data

[63] Continuation of Ser. No. 42,874, May 29, 1979, abandoned.

[51] Int. Cl.$^4$ .................... A61K 31/04; A61K 9/22
[52] U.S. Cl. .................................. 424/81; 424/435
[58] Field of Search .................. 424/19, 22, 78, 81, 424/435

[56] References Cited

U.S. PATENT DOCUMENTS

| | | | |
|---|---|---|---|
| 3,429,308 | 2/1969 | Russell | 424/14 |
| 3,444,858 | 5/1969 | Russell | 424/28 |
| 3,870,790 | 3/1975 | Lowey et al. | 424/19 |
| 4,059,686 | 11/1977 | Tanaka et al. | 424/19 |
| 4,226,848 | 10/1980 | Nagai et al. | 424/19 |
| 4,529,589 | 7/1985 | Davydov et al. | 424/81 |

Primary Examiner—Shep K. Rose
Attorney, Agent, or Firm—Burgess, Ryan & Wayne

[57] ABSTRACT

The antianginal film is a plate, 0.1 to 1.5 thick, consisting of a biologically soluble and resolvable carrier, which is a hompolymer of acrylamide or vinylpyrrolidone, or a copolymer thereof with acrylate, containing from 99 to 70 percent by weight of acrylamide with vinylpyrrolidone and from 1 to 30 percent by weight of acrylate having a molecular mass from 50,000 to 1,000,000, and the active principle having antianginal action, the components being taken in the following proportions, in percent by weight:

active substance having antianginal action 3.0–30.0
biologically soluble and resolvable carrier 70.0–97.0

The method of treating ischemic heart disease with the proposed antianginal film by individual doses, consists in that a biologically soluble and resolvable film without any active substance is first applied to a selected site of the mouth mucosa and the time during which this film is fully resolved is determined, this time being characteristic of the period during which the active substance is delivered into the patient's body. Next a medicinal film containing the active substance in the quantity which should be delivered into the patient's body during the time of the film resolution is selected. Finally the film containing the required quantity of the antianginal preparation is applied once or several times, to the selected site of the mouth mucosa to ensure continuous and optimal therapeutic effect during the entire period of the full resolution of the proposed film.

13 Claims, 3 Drawing Figures

ANTIANGINAL FILM AND METHOD OF TREATING ISCHEMIC HEART DISEASE

This application is a continuation of application Ser. No. 42,874, filed May 29, 1979, now abandoned.

FIELD OF THE INVENTION

This invention relates to pharmacy, and more particularly it relates to a new medicinal form, a medicinal film having antianginal action, and the method of treating ischemic heart disease. Said antianginal films are used in cardiology to treat ischemic heart disease.

BACKGROUND OF THE INVENTION

Known in the prior art are antianginal preparations used to arrest attacks of stenocardia containing active substances such as glyceryl trinitrate, isosorbide dinitrate, pentaerythritol tetranitrate, and others.

In addition to said active substances these medicinal preparations contain an inert carrier which is resolved in liquid media of the body. For example, used in the prior art are granules of glyceryl trinitrate containing sugar, starch, and other substances as filling materials (Soviet State Pharmacopoeia, 10th edition).

A disadvantage of the known medicinal preparations containing readily soluble substances, such as sugar, as a filling material, is their low stability in storage and lock of prolonged action.

Also known in the prior art are also tablets of glyceryl trinitrate, prepared by the microcapsulation method (Sustac, Nitrong) wherein the microcapsules perform the function of the carrier material, which is derivatives of cellulose, such methyl cellulose, ethyl cellulose, acetyl cellulose, cellulose acetophthalate, etc. (See U.S. Pat. No. 3,344,029).

Medicinal preparations enclosed in microcapsules start exerting their medicinal action at delayed (to 60 minutes) terms, and this makes it impossible to use them for rapid arresting of stenocardia attacks.

Another disadvantage of capsuled preparations is the relative complexity of their manufacture.

Known widely in the prior art are antianginal preparations manufactured in the form of tablets and drageé. These also include multi-coated pills, containing synthetic polymers, such as polyvinyl alcohol, and a copolymer of polyvinyl alcohol and vinyl acetate, as resolvable carrier material. Synthetic polymers are used to coat tablets or granules so that the rate of liberation of the active principle could be controlled. (French Pat. No. 2,326,933; U.S. Pat. No. 4,012,498).

Also known in the prior art are antianginal preparations in the form of chewing gum containing the active principle and various additives. The base material used in these preparations are polyacrylate polymers (U.S. Pat. No. 3,594,470).

The disadvantage of the known medicinal preparations in the form of tablets pressed with powdered synthetic polymers, and also enclosed in coats of such polymers, is that they can be improperly administered (especially by children who can chew them before swallowing) and hence produce undesirable side effects due to rapid uncontrolled absorption into the body.

The method of treating with such medicinal preparations involves the patient swallowing the medicine (peroral administration), or placing it under the tongue until it fully resolves (sublingual administration) or chewing the gum to ensure gradual administration of the medicine with saliva. In all these administration methods, the active principle penetrates the alimentary tract where it is dissolved, absorbed through the mucosa, and delivered first to the liver and then to the blood circulating system (Petkov, V., "Medicine, Body, Pharmacological Effect", Medicina i Fizkultura, Sofia, 1974).

The general pharmacological disadvantage inherent in all known medicinal antianginal preparations and methods of manufacturing thereof is that when the preparations enter the alimentary tract, and later the liver, the liberated active substance is partially inactivated by the enzymatic systems in the body. The degree of inactivation of the preparations depends on specific characteristics of the living body and its physiological state, which, in general, makes it impossible to dose the medicinal preparation individually so as to ensure its optimum effect.

The main object of this invention is to provide a novel medicinal form, viz., a medicinal film having antianginal action, characterized by prolonged action, improved accuracy of dosage of the active substance, and stability in storage.

The specific object of the invention is to provide a novel medicinal form, namely, antianginal film, which can be used as a medicinal preparation characterized by prolonged action, increased accuracy of dosage of the active principle, and stability in storage.

SUMMARY OF THE INVENTION

Said object has been attained in that an antianginal film, according to the invention, is a 0.1 to 1.5 mm thick film consisting of a biologically soluble and resolvable carrier, namely, a homopolymer of acrylamide or vinyl pyrrolidone, or a copolymer thereof with an acrylate, containing from 99 to 70 percent by weight of acrylamide with vinyl pyrrolidone, and from 1 to 30 percent by weight of an acrylate having a molecular mass from 50,000 to 1,000,000, and an active substance of the antianginal action, said components being taken in the following proportions, in percent by weight:

active substance having antianginal action: 3.0–30.0
biologically soluble and resolvable carrier: 70.–97.0

In order to prolong its action, the medicinal film also contains dispersed solid fat melting from 30° to 50° C., taken in the quantity of from 3 to 30 percent by weight with respect to the weight of all other components.

It is recommended that the antianginal film contain cocoa butter, hydrogenized cotton-seed oil, glycerol laurate or phthalate, as the dispersed solid fat.

The proposed film contains a copolymer of acrylamide, vinylpyrrolidone, and ethyl acrylate, taken in the ratio of 0.6:0.2:0.2 respectively, or a copolymer of acrylamide, vinylpyrrolidone, and butyl acrylate, taken in the ratio of 1.0:0.5:0.2 respectively, or a copolymer of equal quantities of acrylamide, vinylpyrrolidone and ethyl acrylate, as a biologically soluble and resolvable carrier polymer.

The proposed medicinal film preferably contains glyceryl trinitrate, isosorbide dinitrate, or pentaerythritol tetranitrate as the active principle.

The selection of the biologically soluble and resolvable carrier from homopolymers of acrylamide and vinylpyrrolidone and their copolymers with acrylates taken in the specified ratios, depends, according to the invention, on the ability of said polymers to dissolve in liquid media of the body, their harmlessness, and ability to form labile complex bonds with the active principle of the preparation. Solid fats incorporated in the proposed medicinal film, regulate its hydrophobic properties to control the rate of liberation of the active principle from the swollen medicinal film.

The proposed antianginal film can be taken in capsules or be applied to the mouth mucosa. The latter method of administration is a novel method and has not been described in the literature. Its makes it possible to treat ischemic heart disease by individual doses.

According to the invention, the method of treating ischemic heart disease with the proposed antianginal film by individual doses, consists in that a film of a biologically soluble and resolvable carrier polymer containing no active principle of antianginal action, is first applied to a chosen site of the mouth mucosa of the patient, and the time of resolution of the film is determined. This time characterizes the possible time during which the active substance will pass to the body. Next a film is selected containing that amount of the active principle which should be given to the patient during the time of resolution. Finally, said film containing the required amount of the antianginal preparation is applied (once or repeatedly) to the chosen site of the mouth mucosa of the patient to ensure continuous and optimal therapeutic effect during the entire period of dissolution of said film.

The main advantage of the proposed method of treating ischemic heart disease is that the active principle is delivered directly into the systemic blood flow bypassing the liver, the preparation intake being uniform in the course a prolonged period of time.

DETAILED DESCRIPTION OF THE INVENTION

Antianginal films were tried in a clinic. The clinical trials had the following objects: (1) to carry out comparative studies of pharmacodynamics of the antianginal film containing glyceryl trinitrate and the known preparation Sustac as the active substance, both preparations being given per os; (2) to study the pharmacodynamics of the proposed antianginal film, containing glyceryl trinitrate, by applying it to the mouth mucosa, and tablets of glyceryl trinitrate given sublingually.

The pharmacodynamic effects were assessed by the central and peripheral, hemodynamic indices, and also by the changes in tolerance to physical exercise. Earlier we had established the correlation ($r=0.81\pm0.06$; $p<0.001$) between the dynamics (under the effect of nitrates) of the peripheral and central blood circulation indices and the results of the ECG-monitoring with controlled physical load. This helped us judge the efficacy of the proposed medicinal film containing glyceryl trinitrate by studying analogous hemodynamic parameters.

The proposed medicinal film containing glycerol trinitrate was studied on 23 male patients aging from 37 to 62 (average age, 48) with ischemic heart disease manifested in strain stenocardia, with 1 to 15 attacks a day; seven patients had myocardial infarction in the past (with ECG records). The clinical manifestations of the disease averaged from five months to 12 years. 21 patients were tested by bicycle ergometry: 12 of them showed low tolerance for physical load, medium tolerance was in 5 and high in 4 patients. The mean load in the test group was 421.4 kg-m/min; the work done was 2260 kg-m. Thirteen patients were examined by coronary angiography. Four patients had three main branches of the coronary arteries affected; two branches were affected in one patient, and one branch in four patients; no local stenoses of the coronary vessels were found in the remaining three patients. Three patients had initial signs of cardiac insufficiency. Patients with marked arterial hypertension were not studied.

The following study methods were used: finger impedance plethysmography (FIP), impedance cardiography, ECG-monitoring with controlled physical load, and bicycle ergometry.

FIP was used to assess the peripheral vascular action of the medicinal film containing glyceryl trinitrate by the size of the first negative wave "b" on the first derivative of plethysmogram curve (b). This value was expressed in $10^{-2}$ Ohm/sec.

Impedance-cardiography was used to determine the stroke volume of the heart, from which the stroke index (ml/sq.m) was determined.

ECG-monitoring with controlled physical load was used to study the dynamics of the depression of the ST segment under standard physical loads during many-hour ECG-monitoring with a portable monitor with subsequent computer analysis of the electrocardiogram. At one-hour intervals, the patient was given by the doctor a specially selected standard physical load and the action of the proposed medicinal film containing glyceryl trinitrate was assessed by the decrease in the depression of the ST segment (as compared with the initial one).

The index of ST(D) segment standard depression, characterizing the change in the depression per pulse increment unit was used to assess the efficacy of the proposed medicinal film.

During the bicycle ergometry, we increased the continuous load in steps, beginning with 150 kg-m/min for three minutes, with subsequent 100 percent increase in the load. ECG was taken with 12 standard leads; the arterial pressure and the respiration rate were measured at the second minute of each load step. The load continued (in the absence of contraindications) until horizontal or down-sloping depression of the segment ST to less than 1 mm was attained or until attack of angina pectoris developed. The following indices were analyzed: intensity of the load and the volume of the work done; pulse rate and arterial pressure at the initial and at the peak load: time of continuous work on the bicycle ergometer until signs of myocardial ischemia developed.

Drug thereapy was suspended 24 hours before the tests (except glyceryl trinitrate for sublingual administration to arrest angina pectoris attacks). The initial indices of FIP, the impedance cardiographic indices and arterial pressure were recorded in 2–3 hours after a light breakfast. During ECG-monitoring tests, each patient was given a specially selected starting physical load.

On the first day of the studies, all patients were tested for sensitivity to nitrates by sublingual doses of 0.5 mg of glyceryl trinitrate in tablets. Patients who showed low tolerance for nitrates were later given Sustac, (6.4 mg of glyceryl trinitrate) or tablets of glyceryl trinitrate (6.0 mg), while patients with high tolerance for nitrates were given Sustak (12.8 mg) or glyceryl trinitrate tablets (9.0 mg). The dose of the proposed medicinal film containing glyceryl trinitrate for application to the mouth mucosa was determined depending on the time of resolution of the carrier without the active principle (glyceryl trinitrate). To determine individual doses of the medicinal film containing glyceryl trinitrate, the doctor applied the polymer carrier (without the active principle) to the mouth mucosa, for example in the region of the upper gum above the canines or premolars, and determined the time during which the film fully resolved. Next he chose the medicinal film containing the required amount of glyceryl trinitrate which would ensure continuous and optimal therapeutic effect during the time of full resolution of the film.

Approximate calculation: 0.3–0.5 mg of glyceryl trinitrate per each 30 minutes of film resolution. The selected type of the medicinal film containing the corresponding dose of glyceryl trinitrate, namely 1 mg (for 60–90 minutes of resolution), or 2 mg (for 2–3 hour resolution), or 3 mg (to 6 hours of film resolution) can then be practiced by the patient himself, who applies the film to the gum mucosa on the same or the opposite side.

Each pharmacodynamic study was continued from 6 to 7 hours. The hemodynamic indices were recorded at one-hour intervals at standard conditions. In complex studies with ECG-monitoring, the physical load followed the recording of the hemodynamic indices.

Bicycle ergometry was carried out by the double blind method during two days, in 1.5 hour intervals after applying the film-carrier or the film containing glyceryl trinitrate onto the gum. The standard conditions of imposing dosed physical loads were observed during the tests.

On the days of studies, food and physical activity of patients were strictly controlled.

The results of studies were treated statistically by the Student's method.

Comparative pharmacodynamic studies of Sustac (6.4 and 12.8 mg) and of the medicinal film containing glyceryl trinitrate in capsules for peroral administration (6.0 and 9.0 mg) were carried out on ten patients. The materials pertaining to one patient were excluded from statistical analyses because of technical artefact of FIP. Tables 1 and 2, which follow below, give the hemodynamic indices obtained in the course of studies after taking one dose of Sustac or the medicinal film containing glyceryl trinitrate in capsules. The group of patients who were given 12.8 mg of Sustac and 9.0 mg of glyceryl trinitrate in capsules in the proposed medicinal film, contained only persons with low sensitivity to glyceryl trinitrate. The mean hemodynamic effect of this preparation in the selected group of patients only insignificantly differed from the similar effect in the group of patients who were given smaller doses (6.4 and 6.0 mg respectively). The effects differed insignificantly in both magnitude and duration.

Systolic arterial pressure (SAP) was lower compared with the initial level and remained so for three hours after taking Sustac (7.2±1.7 percent maximum), and for two hours after taking the medicinal film containing glycerol trinitrate (8.3±3.4 percent maximum), but the lowered SAP was not statistically proven.

The stroke index, according to impedance cardiography, decreased distinctly in the course of the first few minutes after administrations of Sustac and remained so for 4–5 hours. The proposed medicinal film containing glyceryl trinitrate in capsules decreased the stroke index only after 30 minutes and this effect persisted for four hours. The delayed action probably depended on the time of the capsule dissolution in the alimentary tract. The maximum decrease in the stroke index was more significant after the administration of the medicinal film containing glyceryl trinitrate (27.4±3.2 in 60 minutes) compared with the corresponding magnitude attained after the administration of Sustac (24.7±5.6 in 30 minutes).

The amplitude of the wave "b", according to FIP, increased to the maximum extent in the first 10–30 minutes after the administration of Sustac and the initial level was restored in 6 hours. With the proposed medicinal film containing glyceryl trinitrate the maximum changes were observed in longer lapses of time (in 2–3 hours) and the initial indices were restored in shorter time (by the fifth hour).

Figure 1:
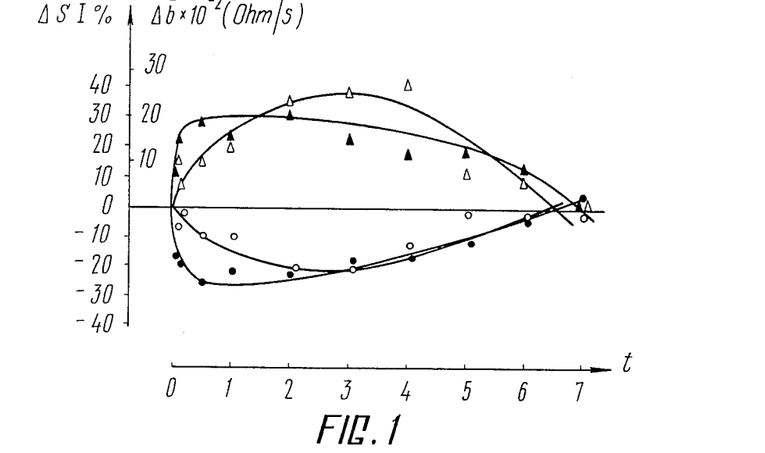
Figure 2:
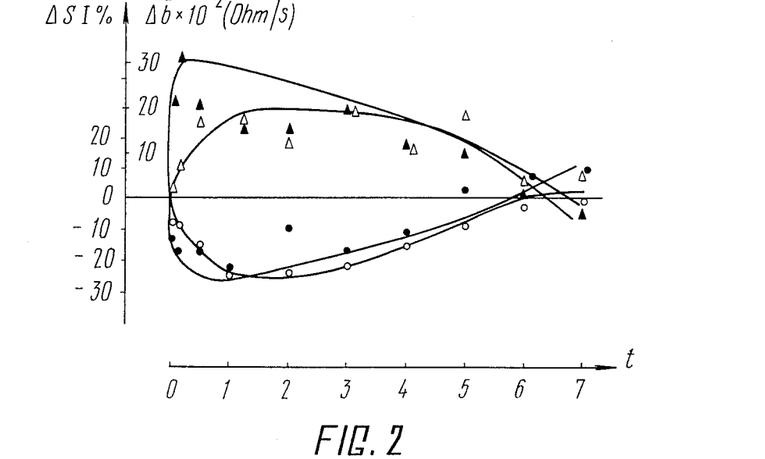

Hemodynamic indices obtained for said studies, are given in FIGS. 1 and 2. FIG. 1 illustrates pharmacodynamics of Sustac (6.4 mg) and the medicinal film containing glycerol trinitrate (6.0 mg), taken per os, according to impedance-cardiography and finger impedance ethysmography TIP. Mean data are presented. Plotted against the axis of ordinates is $\Delta SI\%$—variations in the stroke index, in percent of the starting value (figures to the left of the axis); $\Delta b \times 10^{-2}$ ohm/sec—the change in the value of the first negative wave "b" on the curve of the first FIP derivative, with respect to the initial value, expressed in ohm/sec with the scale factor $10^{-2}$ introduced for the sake of convenience of calculations (figures to the right of the axis). Plotted against the axis of abscissas is time (t) in hours. Circles and triangles are used for the proposed medicinal film containing glyceryl trinitrate and shaded circles and triangles for Sustac.

FIG. 2 shows pharmacodynamics of Sustac (12.8 mg) and the proposed medicinal film containing glyceryl trinitrate (9 mg), taken per os, according to impedance cardiography and FIP. Mean data are given. Symbols and designations used in the figure are the same as in FIG. 1.

The comparison shows that the hemodynamic effect of the proposed medicinal film containing glyceryl trinitrate is similar to that of Sustak.

The pulse rate and the diastolic pressure did not significantly change except for two cases where tachycardia developed during the first 15 minutes after the administration of Sustak.

Side effects were observed in five patients after the administration of Sustac (dizziness in two and headache in three) and only in three patients (headache) after the administration of the proposed medicinal film containing glyceryl trinitrate.

Pharmacodynamics of the proposed medicinal film containing glyceryl trinitrate applied to the mouth mocosa and of glyceryl trinitrate in tablets, given sublingually, were studied. The investigations showed that the time of resolution of the carrier film (without glyceryl trinitrate) varies significantly in different persons: from 30 minutes to 6.5 hours, and in some cases even to 10 hours. It follows therefore that one and the same medicinal film containing, for example, 2 mg, will cause grave side effects from overdosage (hypotension, collapse, etc) in persons in whom the time of full resolution of the film is 30–45 minutes, while the same film will give insufficient dose to patients in whom the film will resolve only in six and more hours, the adequate dose of the preparation being given only to patients in whom the film will resolve in 2–3 hours.

Pharmacodynamic studies of the proposed medicinal film containing glyceryl trinitrate in doses of 1, 2 and 3 mg, (depending on the time of resolution of the film without glyceryl trinitrate) were carried on 17 patients with ischemic heart disease with angina pectoris. The film was applied to the mount mucosa. Glyceryl trinitrate preparations did not produce any response in one patient who was therefore removed from the further analysis. The results of the studies are given in Tables 3 and 4 which follow hereinafter.

The proposed medicinal film containing 1 mg of glyceryl trinitrate was given to 9 patients in whom the film resolved in 1.5 to 2.5 hours. Systolic arterial pressure diminished, compared with the initial level, in the course of 15 minutes following sublingual administration of glyceryl trinitrate (maximum by $8.3 \pm 2.2$ percent at the fifth minute) and in the course of two hours with applying the film on the mouth mucosa (maximum by $7.9 \pm 1.6$ percent at the 90th minute). The changes in the systolic arterial pressure were however not reliably proved statistically.

The stroke index decreased after sublingual use of glyceryl trinitrate in tablets in the course of 20 minutes (maximum by $40.3 \pm 2.9$ percent by the fifth minute) and in the course of three hours with the application of the medicinal film to the mouth mucosa (maximum by $34.9 \pm 4.1$ percent by the 60th minute).

The amplitude of the wave "b" in FIP increased to its maximum in the course of the first five minutes following sublingual use of glyceryl trinitrate in tablets and restored to the initial level in thirty minutes. When the proposed film was applied to the mouth mucosa, the amplitude of the wave "b" increased immediately and returned to the initial level in three hours.

Thus, the medicinal film containing glyceryl trinitrate produced a marked effect on the hemodynamics in the first minutes after its application to the mouth mucosa, and the effect persisted for about three hours. The intensity of the hemodynamic effect of the medicinal film was similar to that of glyceryl trinitrate tablets given sublingually, but the intense effect perisited for much longer periods with the proposed medicinal film.

TABLE 1

Dynamics of systolic arterial pressure (SAP), stroke index (SI), amplitude of wave "b" in FIP after administration of Sustac (6.4 mg) and proposed medicinal film containing glyceryl trinitrate (6 mg) per os

| | | | Initial indices | Mean deviation from initial level Time after administration, min | | | | |
|---|---|---|---|---|---|---|---|---|
| | | | | 5 | 10 | 30 | 60 | 120 |
| First group (n = 4) | Sustac, 6.4 mg | SAP | 129.2 | $-4.7 \pm 2.7$ | $-7.2 \pm 1.7$ | $-4.6 \pm 2.2$ | $-8.2 \pm 11.4$ | $-5.0 \pm 2.1$ |
| | | SI | 26.8 | $-16.3 \pm 9.6$ | $-18.2 \pm 9.4$ | $-24.7 \pm 5.6$ | $-20.0 \pm 5.2$ | $22.7 \pm 4.3^{(x)}$ |
| | | "b" | 16.2 | $8.0 \pm 7.3$ | $15.0 \pm 10.2$ | $19.0 \pm 13.0$ | $16.0 \pm 9.0$ | $20.0 \pm 11.4$ |
| | Proposed medicinal film containing 6.0 mg of glyceryl trinitrate | SAP | 128.7 | $-3.0 \pm 1.0$ | $-1.5 \pm 1.9$ | $-8.3 \pm 3.4$ | $-3.4 \pm 3.6$ | $4.7 \pm 2.5$ |
| | | SI | 29.0 | $-7.5 \pm 7.6$ | $-0.5 \pm 5.2$ | $-10.5 \pm 9.0$ | $-10.0 \pm 3.1$ | $-21.7 \pm 2.8^{(x)}$ |
| | | "b" | 12.5 | $12.5 \pm 7.6$ | $8.7 \pm 3.8$ | $10.0 \pm 5.0$ | $14.0 + 2.4^{(x)}$ | $24 \pm 5.1^{(x)}$ |

| | | | Initial indices | Mean deviation from initial level Time after administration, min | | | | |
|---|---|---|---|---|---|---|---|---|
| | | | | 180 | 240 | 300 | 360 | 420 | 480 |
| First group (n = 4) | Sustac, 6.4 mg | SAP | 129.2 | $-7.0 \pm 1.9$ | $-4.7 \pm 3.2$ | $-2.1 \pm 4.0$ | $-1.2 \pm 2.8$ | $+0.9 \pm 1.7$ | $+6.0 \pm 2.0$ |
| | | SI | 26.8 | $-18.2 \pm 8.6$ | $-17.2 \pm 4.6$ | $-12.7 \pm 3.4$ | $-4.7 \pm 3.0$ | $+3.7 \pm 2.2$ | $+14.0 \pm 1.0$ |
| | | "b" | 16.2 | $15.0 \pm 2.0^{(xx)}$ | $12.5 \pm 3.2^{(x)}$ | $13.0 \pm 2.8^{(x)}$ | $9.0 \pm 5.2$ | $-1.6 \pm 1.7$ | $-5.0 \pm 0$ |
| | Proposed medicinal film containing 6.0 mg of glyceryl trinitrate | SAP | 128.7 | $-4.4 \pm 3.3$ | $-3.7 \pm 5.5$ | $-0.9 \pm 1.5$ | $+2.2 \pm 9.8$ | $+1.5 \pm 3.5$ | $-7.0$ |
| | | SI | 29.0 | $-22.5 \pm 2.9^{(xx)}$ | $-12.7 \pm 3.5$ | $-2.0 \pm 3.6$ | $-4.3 \pm 4.7$ | $+0.7 \pm 3.8$ | $+4.0$ |
| | | "b" | 12.5 | $26.0 + 11.5$ | $29.0 \pm 9.0$ | $6.0 \pm 5.1$ | $5.0 \pm 0$ | $2.5 \pm 2.5$ | $5.0$ |

Deviations in "b" are given in Ohm/sec; the other indices are in percent;
n is the number of patients;
$^{(x)}p < 0.05$;
$^{(xx)}p < 0.01$

TABLE 2

Dynamics of systolic arterial pressure (SAP), stroke index (SI), and amplitude of wave "b" in FIP after peroral administration of Sustac (12.8 mg) and proposed medicinal film containing 9 mg of glyceryl trinitrate

| | | | Initial indices | Means deviation from initial level Time after administration, in min | | | | |
|---|---|---|---|---|---|---|---|---|
| | | | | 5 | 10 | 30 | 60 | 120 |
| Second group (n = 5) | Sustac, 12.8 mg | SAP | 122.0 | $-6.9 \pm 4.1$ | $-7.3 \pm 4.1$ | $-4.4 \pm 4.7$ | $-4.8 \pm 2.5$ | $3.8 + 5.1$ |
| | | SI | 31.4 | $-12.6 \pm 4.4^{(x)}$ | $-16.4 \pm 5.1^{(x)}$ | $-15.6 \pm 5.7$ | $-22.8 \pm 2.8^{(xx)}$ | $9.2 + 4.7$ |
| | | "b" | 19.5 | $23.0 \pm 7.8$ | $32.0 \pm 12.4$ | $21.0 \pm 9.7$ | $15.0 \pm 6.8$ | $5.0 + 9.7$ |
| | Proposed medicinal film containing 9 mg of glyceryl trinitrate | SAP | 120.6 | $0 \pm 1.3$ | $-1.0 \pm 1.9$ | $-3.0 \pm 1.4$ | $-7.0 \pm 2.5$ | $-5.1 + 3.1$ |
| | | SI | 31.8 | $-8.6 \pm 5.7$ | $-9.4 \pm 4.6$ | $-16.8 \pm 4.5^{(x)}$ | $-27.4 \pm 3.2^{(x)}$ | $-25.0 + 1.6^{(xxx)}$ |
| | | "b" | 16.0 | $2.5 \pm 3.2$ | $8.0 \pm 3.4$ | $18.0 \pm 5.4^{(x)}$ | $18.0 \pm 6.0^{(x)}$ | $13.0 + 2.0^{(x)}$ |

| | | | Initial indices | Means deviation from initial level Time after administration, in min | | | | |
|---|---|---|---|---|---|---|---|---|
| | | | | 180 | 240 | 300 | 360 | 420 | 480 |
| Second group | Sustac, 12.8 mg | SAP | 122.0 | $-4.1 + 4.0$ | $-1.8 + 2.8$ | $-0.8 + 2.3$ | $+8.2 + 2.6$ | $+13.7 + 3.5$ | — |
| | | SI | 31.4 | $-17.5 + 4.3$ | $-11.4 + 5.6$ | $+13.3 + 3.8$ | $+5.4 + 7.8$ | $+8.6 + 5.0$ | $+7.0$ |

TABLE 2-continued

Dynamics of systolic arterial pressure (SAP), stroke index (SI), and amplitude of wave "b" in FIP after peroral administration of Sustac (12.8 mg) and proposed medicinal film containing 9 mg of glyceryl trinitrate

| (n = 5) | | | | | | | | | |
|---|---|---|---|---|---|---|---|---|---|
| | | "b" | 19.5 | 24.0 + 10.2 | 13.6 + 6.6 | 10.0 + 6.9 | −1.1 + 3.7 | −3.6 + 5.9 | 0 + 5.0 |
| | Proposed medicinal | SAP | 120.6 | −5.0 + 2.2 | −1.3 + 4.4 | +2.4 + 2.2 | +3.8 + 2.1 | +5.3 + 2.7 | +16.0 |
| | | SI | 31.8 | −23.0 + 1.9$^{(xxx)}$ | −16.6 + 2.1$^{(xx)}$ | −8.4 + 2.7 | −3.2 + 3.4 | −2.0 + 2.2 | +10.0 |
| | film containing 9 mg of glyceryl trinitrate | "b" | 16.0 | 18.0 + 4.4$^{(x)}$ | 10.0 + 2.2 | 18.0 + 5.1$^{(x)}$ | 5.0 + 5.0 | 0 | |

Deviations in "b" are given in Ohm/sec; the other indices are in percent;
n is the number of patients
$^{(x)}p < 0.05$;
$^{(xx)}p < 0.01$;
$^{(xxx)}p < 0.001$ Medicinal film containing 2 mg of glyceryl trinitrate was given to 7 patients in whom the mean resolution time of the film carrier (without glyceryl trinitrate) was from 2.5 to 4 hours. The stroke index, wave "b" in FIP were proved to change and the indices were close to the data obtained with the dose of 1.0 mg. There were no reliable proofs of changes in the systolic arterial pressure. In two cases the hemodynamic effect was observed for four hours which fully coincided with the time of resolution of the corresponding film without glyceryl trinitrate in these patients.

Figure 3:
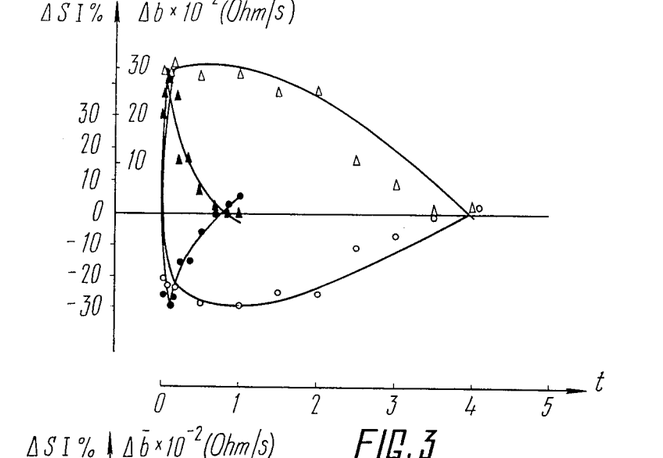
Figure 4:
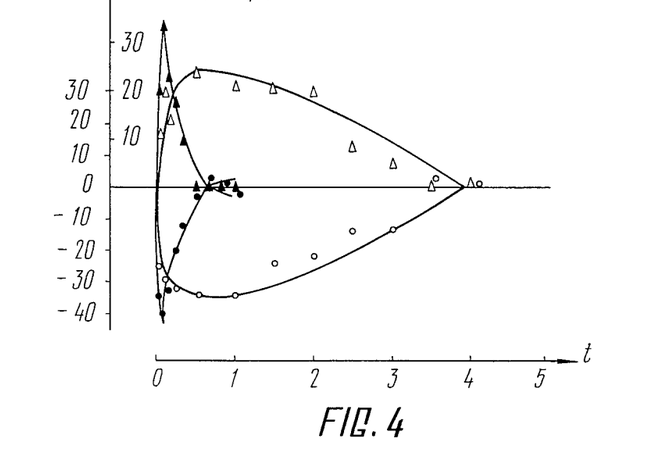

The results of said studies are given in FIGS. 3 and 4.

FIG. 3 shows the pharmacodynamics of glycerol trinitrate in tablets (0.5 mg) given sublingually and the proposed medicinal film containing glyceryl trinitrate (2 mg) when applied to the mouth mucosa (according to impedance cardiography and FIP data). Mean data are given. The designations and symbols used in the figure are same as in FIG. 1.

FIG. 4 shows pharamcodynamics of glyceryl trinitrate tablets (0.5 mg) given sublingually and of the proposed medicinal film containing 1 mg of glyceryl trinitrate when applied to the mouth mucosa (impedance cardiography and FIP data). Mean data are given. The symbols and designations are the same as in FIG. 1.

ECG-monitoring with controlled physical load was carried out as follows. Dynamics of depression of the ST segment was studied in ten patients to whom controlled physical loads were given after giving placebos (6 patients) and the proposed film containing 2 mg of glyceryl trinitrate (8 patients). The data obtained indicate that after applying the medicinal film containing glyceryl trinitrate to the mouth mucosa, the ST segment depression ($\Delta D\%$) was reliably proved to decrease in the course of three hous with application of equal loads, the maximum effect being attained at the 30–60th minute. The ST segment depression variation in patients to whom placebos had been given did not exceed 4 percent. The results of the tests are given in Table 5 and FIG. 5.

Figure 5:
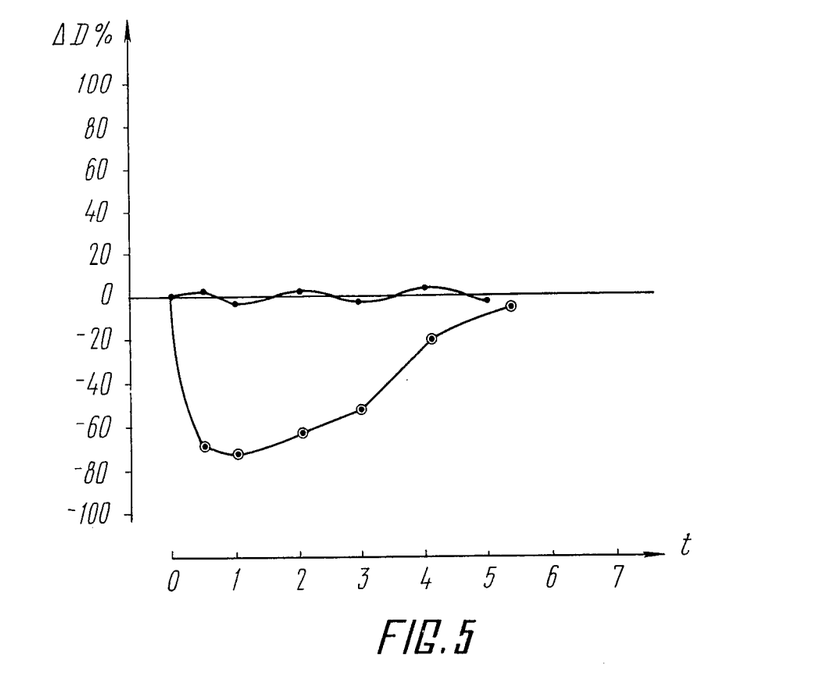

FIG. 5 shows the dynamics of the ST segment depression under standard physical loads after application of the proposed medicinal film containing glyceryl trinitrate to the mouth mucose (2 mg), according to ECG-monitoring. Mean data are given.

Plotted against the axis of ordinates is the change in the ST segment depression ($\Delta D\%$) after application of the film without glyceryl trinitrate (placebo), designated by a curve with dots; or after applying the medicinal film containing glyceryl trinitrate to the mouth mucosa (designated by a curve with dots in circles).

Time (t) in minutes, after the administration of the preparation is plotted against the axis of abscissas.

Tolerance for physical load with bicycle ergometer was tested in eleven patients to whom a placebo was given after 1 or 2 mg of the medicinal film containing glyceryl trinitrate. Mean results of the bicycle ergometric test given in Table 6 show the increasing tolerance for physical load and increasing activity in patients to whom the true preparation was given. In two cases we failed to complete the predetermined work because of general fatique although the patients were given the true preparation, and the test was discontinued with patients to whom the placebo was given (although the load was lessened) because signs of myocardial ischemia developed.

The studies carried out showed the efficacy of the proposed medicinal film containing glyceryl trinitrate both given per os and glued to the mouth mucosa to patients with ischemic heart disease. Comparative pharmacological studies of the medicinal film containing glyceryl trinitrate for peroral use and of Sustac showed that both preparations produce similar effect on the studied hemodynamic parameters: stroke index, systolic arterial pressure, and peripheral vasodilation. Objective hemodynamic measurements showed that the medicinal film containing glyceryl trinitrate, given per os, produces a specific pharmacodynamic effect in the course of 4–4.5 hours (like Sustac). When considering mean data, important information concerning individual response to the therapy should also be included. For example, the indices were quite varied after the administration of 12.8 mg of Sustac, which was associated with individual response of patients to the preparation. More uniform results were obtained with the proposed film containing glyceryl trinitrate applied to the mouth mucosa of the patients. The direct uptake of glyceryl trinitrate by the body, bypassing the liver, ensures a pronounced pharamcodynamic effect which manifests practically instantaneously and persists for 2.5-4 hours. This method of administration of the active principle has the following advantages: a reliable and pronounced hemodynamic effect is attained with markedly lower doses of the active substance; patients do not complain of any inconveniences and well tolerate this medicinal form; a great advantage of the new form is that it is possible to control the uptake of glyceryl trinitrate whenever necessary; it is easy to discontinue the uptake of the preparation by removing the unresolved film in cases where it becomes necessary, or, on the contrary, it is easy to renew the thereby, the therepautic effect being attained practically instantaneously.

TABLE 3

Dynamics of systolic arterial pressure (SAP), Stroke index (SI), and amplitude of wave "b" after application of medicinal film containing glyceryl trinitrate to mouth mucosa

| | | Initial indices | Mean deviations from initial level in minutes | | | | |
|---|---|---|---|---|---|---|---|
| | | | 2 | 5 | 10 | 30 | 60 |
| Group 1 (n = 9) film containing 1 mg of glyceryl trinitrate | SAP | 134.3 | −2.7 ± 0.6 | −2.8 ± 0.7 | −4.2 ± 1.3 | −7.3 ± 0.8 | −7.8 ± 1.6 |
| | SI | 28.8 | −25.0 ± 5.5$^{xx}$ | −27.8 ± 4.1$^{xxx}$ | −32.2 ± 3.5$^{xxx}$ | −33.6 ± 3.1 | −34.9 ± 4.1$^{xxx}$ |
| | "b" | 14.2 | 13.1 ± 4.0$^{x}$ | 20.3 ± 4.6$^{xx}$ | 15.3 ± 2.0$^{xxx}$ | 24.2 ± 4.8$^{x}$ | 22.2 ± 5.9$^{xx}$ |
| Group 2 (n = 7) film containing 2 mg of glyceryl trinitrate | SAP | 125.3 | −3.1 ± 1.2 | 6.2 ± 1.3 | −5.0 ± 3.8 | −5.9 ± 1.0 | −5.4 ± 1.6 |
| | SI | 27.9 | −21.0 ± 1.5$^{xxx}$ | −23.2 ± 3.8$^{xx}$ | −23.4 ± 2.8$^{xxx}$ | −28.3 ± 6.1$^{xx}$ | −28.9 ± 5.6$^{xx}$ |
| | "b" | 0.15 | 28.9 ± 6.0$^{xx}$ | 28.3 ± 4.4$^{xxx}$ | 31.4 ± 4.3$^{xxx}$ | 28.6 ± 4.4$^{xx}$ | 29.3 ± 3.0$^{xxx}$ |

| | | Initial indices | Means deviations from initial level in minutes | | | | | |
|---|---|---|---|---|---|---|---|---|
| | | | 90 | 120 | 150 | 180 | 210 | 240 |
| Group 1 (n = 9) film containing 1 mg of glyceryl trinitrate | SAP | 134.3 | −7.9 ± 1.6 | −3.8 ± 0.8 | −0.5 ± 1.0 | −0.3 ± 1.2 | +1.2 ± 2.0 | +2.2 ± 1.6 |
| | SI | 28.8 | −25.4 ± 5.0$^{xx}$ | −23.3 ± 4.6$^{xx}$ | −14.2 ± 6.7 | −14.3 ± 6.1 | +3.2 ± 1.8 | +1.0 ± 4.4 |
| | "b" | 14.2 | 20.0 ± 7.6$^{x}$ | 20.6 ± 7.0$^{xx}$ | 7.5 ± 2.8 | 5.0 ± 2.4 | 0 ± 1.4 | 1.5 ± 4.1 |
| Group 2 (n = 7) film containing 2 mg of glyceryl trinitrate | SAP | 125.3 | −6.0 ± 1.5 | −5.4 ± 1.2 | −5.1 ± 1.9 | −0.6 ± 0.8 | +2.6 ± 1.7 | +2.6 ± 1.8 |
| | SI | 27.9 | −27.0 ± 6.2$^{x}$ | −26.4 ± 7.0$^{x}$ | −19.4 ± 3.9$^{x}$ | −12.3 ± 4.4 | −3.7 ± 5.2 | −3.4 ± 5.6 |
| | "b" | 0.15 | 25.5 ± 7.3$^{x}$ | 25.8 ± 8.1$^{x}$ | 11.0 ± 1.0$^{xxx}$ | 7.1 ± 2.6 | 0 ± 2.9 | 2.0 ± 2.0 |

Notes:
deviations in "b" are given in Ohm/sec; the other indices are in percent
$^{x}$P < 0.05;
$^{xx}$P < 0.01;
$^{xxx}$P < 0.001
n is the number of patients

TABLE 4

Dynamics of systolic arterial pressure (SAP), stroke index (SI), and wave "b" amplitude in TRP after sublingual administration of glyceryl trinitrate tablet (0.5 mg)

| | | | Initial indices | Means deviation from initial level Time after administration, min | | | |
|---|---|---|---|---|---|---|---|
| | | | | 2 | 5 | 10 | 15 |
| Group 1 (n = 9) | Tablets of glyceryl trinitrate, 0.5 mg | SAP | 130.8 | −7.1 ± 1.5 | −8.3 ± 2.2 | −4.2 ± 1.6 | −2.7 ± 1.7 |
| | | SI | 28.8 | −34.3 ± 4.6$^{xxx}$ | −40.3 ± 2.9 | −33.8 ± 4.3$^{xxx}$ | −20.0 ± 3.9$^{xx}$ |
| | | "b" | 18.6 | 21.0 ± 5.8$^{x}$ | 34.0 ± 8.2$^{xx}$ | 24.0 ± 5.9$^{xx}$ | 18.0 ± 4.6$^{xx}$ |
| Group 2 (n = 7) | | SAP | 129.3 | −8.7 ± 2.6 | −9.6 ± 2.1 | −7.9 ± 1.8 | −3.5 ± 3.3 |
| | | SI | 30.5 | −26.3 ± 5.6$^{xx}$ | −29.6 ± 5.4$^{xx}$ | −28.4 ± 5.7$^{xx}$ | −16.1 ± 7.7 |
| | | "b" | 16.0 | 20.0 ± 5.3$^{x}$ | 28.0 ± 5.4$^{xx}$ | 22.0 ± 4.3$^{xx}$ | 11.0 ± 5.5 |

| | | | Initial indices | Means deviation from initial level Time after administration, min | | | | |
|---|---|---|---|---|---|---|---|---|
| | | | | 20 | 30 | 40 | 50 | 60 |
| Group 1 (n = 9) | Tablets of glyceryl trinitrate, 0.5 mg | SAP | 130.8 | +0.8 ± 2.1 | +0.4 ± 1.1 | +2.1 ± 1.1 | +2.3 ± 0.2 | +3.0 ± 1.0 |
| | | SI | 28.8 | −12.0 ± 4.0 | −3.1 ± 2.0 | +3.7 ± 2.4 | +1.0 ± 4.2 | −2.3 ± 5.0 |
| | | "b" | 18.6 | 10.0 ± 3.0$^{x}$ | 0 ± 3.0 | 0 ± 1.7 | 0 ± 2.0 | 0 ± 5.0 |
| Group 2 (n = 7) | | SAP | 129.3 | −6.1 ± 3.4 | −3.7 ± 4.1 | +0.6 ± 3.3 | −1.7 ± 2.7 | −2 ± 0 |
| | | SI | 30.5 | −16.1 ± 3.9$^{x}$ | −6.0 ± 3.9 | +0.3 ± 3.5 | +2.2 ± 3.9 | +4.7 ± 5.9 |
| | | "b" | 16.0 | 12.0 ± 3.5$^{x}$ | 5 ± 2.5 | 2.0 ± 0.9 | 0 ± 1.6 | 0 ± 1.7 |

Deviations in "b" are given in Ohm/sec; the other indices are given in percent;
n is the number of patients;
$^{x}$P < 0.05;
$^{xx}$P < 0.01;
$^{xxx}$P < 0.001

TABLE 5

Pharmacodynamics of medicinal film containing glyceryl trinitrate when applied to mouth mucosa (mean data of ECG-monitoring)

| | | Time after administration, min. | | | | | | |
|---|---|---|---|---|---|---|---|---|
| | | 0 | 30 | 60 | 120 | 180 | 240 | 300 |
| Placebo (n = 6) | $P_{max}$ (st/min) | 88.5 ± 3.2 | 94.0 ± 3.5 | 90.5 ± 4.2 | 86.6 ± 4.6 | 87.8 ± 3.9 | 86.6 ± 3.4 | 90.5 ± 4.6 |

TABLE 5-continued

Pharmacodynamics of medicinal film containing glyceryl trinitrate when applied to mouth mucosa (mean data of ECG-monitoring)

| | | Time after administration, min. | | | | | | |
|---|---|---|---|---|---|---|---|---|
| | | 0 | 30 | 60 | 120 | 180 | 240 | 300 |
| | $ST_{max}$ (mm) | 1.3 ± 0.3 | 1.2 ± 0.1 | 1.2 ± 0.1 | 1.2 ± 0.2 | 1.3 ± 0.2 | 1.3 ± 0.2 | 1.2 ± 0.2 |
| | D (u) | 4.2 ± 0.9 | 3.3 ± 0.6 | 4.7 ± 1.1 | 4.2 ± 1.1 | 4.2 ± 0.9 | 3.6 ± 0.6 | |
| | D (%) | 0 | 3.6 ± 5.6 | −1.0 ± 3.8 | 0.1 ± 3.0 | −0.4 ± 3.4 | 2.8 ± 3.0 | −1.4 ± 4.2 |
| Medicinal film containing glyceryl trinitrate (n = 8) | $P_{max}$ (st/min) | 101.8 ± 3.3 | 100.1 ± 2.6 | 95.1 ± 2.4 | 95.5 ± 2.1 | 97.4 ± 3.6 | 99.5 ± 3.8 | 107.2 ± 6.3 |
| | $ST_{max}$ (mm) | 1.9 ± 0.31 | 0.6 ± 0.22 | 0.4 ± 0.13 | 0.7 ± 0.17 | 1.0 ± 0.3 | 1.6 ± 0.35 | 2.0 ± 0.2 |
| | D (u) | 6.6 ± 0.97 | 2.1 ± 0.70 | 1.9 ± 0.65 | 2.7 ± 0.7 | 3.6 ± 1.00 | 5.7 ± 1.3 | 5.8 ± 0.9 |
| | D (%) | 0 | −70 ± 7.2$^{xx}$ | −74.0 ± 6.8$^{xx}$ | −62.7 ± 7.9$^{xx}$ | −52.6 ± 11.2$^{x}$ | −19.7 ± 7.1 | −4.5 ± 7.8 |

$P_{max}$ is the maximum pulse rate under load;
$ST_{max}$ is the maximum depression depth of segment ST under load;
D is the ST-segment normative depression
$^{x}P < 0.01$;
$^{xx}P < 0.001$;
n is the number of patients

TABLE 6

Comparison of ECG data taken under controlled physical load on bicycles ergometer after giving placebo and medicinal film containing 1 or 2 mg of glyceryl trinitrate (applied to mouth mucosa)

| | Mean load | | Load intensity, | Time of continuous | Heart beat rate | | Arterial pressure | | Criteria for discontinuation of test | |
|---|---|---|---|---|---|---|---|---|---|---|
| n = 11 | kg-m | % | kg-m per min | work, min | initial | under load | initial | under load | AP+ +ST | dyspnea |
| Placebo | 2154 | 100 | 395.4 | 6.6 | 72.3 | 119.8 | 126/78 | 167/97 | 11 | 0 |
| Medicinal film containing glycerol trinitrate | 4425 | 240 | 600.0 | 10.4 | 82.5 | 131.0 | 115/78 | 160/91 | 9 | 2 |

AP means of angina pectoris
ST ↓ is segment ST depressions >1 mm;
n is the number of patients.

The high efficacy of the proposed medicinal form has been proved by the data of the test with physical loads which showed considerable improvement of tolerance for load and increased activity of patients with the medicinal film attached to the mouth mucosa.

Hemodynamic data well agree with the results of ECG-monitoring under repeated standard physical loads, which objectively proves efficacy of the proposed film containing glyceryl trinitrate.

Side effects, which develop during the treatment with the proposed film containing glyceryl trinitrate, are insignificant. Slight pricking at the site of application of the film was reported by 11 patients in the course of the first 10–30 minutes, after which these sensations subside. Nine patients had dizziness, the same as with the use of glycerol trinitrate tablets for sublingual administration.

Individual doses of medicinal films containing other active principles, e.g. isosorbide dinitrate, pentaerythritol tetranitrate, etc., can also be given for application to the mouth mucosa.

The method of individual dosage ensures not only a more prolonged effect of the preparation (in the course of a few hours) but also prevents side effects, such as headache, dizziness, postural hypotonia, or nausea. It is known that like glyceryl trinitrate, isosorbide dinitrate taken per os in the form of tablets is rapidly metabolized in the liver by the enzymatic mechanism, i.e. its biological assimilability with the administration per os is low and differs significantly in various patients. If isosorbide dinitrate is used in the medicinal film as the active substance, it enters the blood circulating system from the mouth mucosa bypassing the liver.

When pentaerythritol tetranitrate tablets are taken per os the major part of the active principle gets into the blood circulating system in inactivated form because of its metabolism in the liver.

The method of individual doses of the medicinal film containing pentaerythritol tetranitrate ensures the delivery of the active substance into the systemic blood circulation bypassing the liver. It considerably prolongs the hemodynamic effect (in the course of several hours) and prevents side effects, such as headache, noise in the ears, dizziness, postural hypotension, diarrhea.

An important advantage of the proposed medicinal film possessing antianginal action is its high adhesion in the swollen state to the mouth mucosa, which makes it possible to attach it to a chosen site of the mucosa where it remains fixed until fully resolved to ensure uniform delivery of the active substance directly into the mucosa and further into the blood circulation system bypassing the gastrointestinal tract to rule out uncontrolled partial inactivation of the active principle.

In contrast to the known carriers, polymer carriers of the proposed medicinal film, on contact with aqueous solutions ensure markedly uniform delivery of the active substance into the body which decreases, or even completely removes side effects, such as headache, or sharp changes in the blood pressure which are otherwise observed with the known antianginal preparations. The uniform liberation of the active principle, for example, of glyceryl trinitrate, from the medicinal film is illustrated in Table 7 which is given below (the data are given in comparison with the known tablets of glyceryl trinitrate).

The method of preparing the antianginal film according to the invention is as follows: Solutions of a biologically resolvable soluble polymer carrier and the active substance are prepared in standard mixers. The solvents should be compatible, or a single solvent should be used to dissolve the active substance and the polymer carrier. The solutions are then put together at the required ratio of the components, air is removed from the solutions in vacuum at room temperature and a film, 0.1 to 1.5 mm thick, is cast on an inert surface by using standard casting equipment. The film is dried at temperatures to 40° C. until the residual amount of the solvent does not exceed 10 percent by weight, and circular plates of the required size are pressed out mechanically. If the medicinal film should contain dispersed fat, it is introduced into the solution containing the active substance and the biologically soluble and resolvable polymer carrier, and the mixture is stirred mechanically, by ultrasound, or by any other known method to ensure uniform distribution of fat in the mixture.

TABLE 7

| Antianginal preparation | Amount of the active substance (in %) liberated in time lapses (min) | | | | |
|---|---|---|---|---|---|
|  | 2 | 5 | 10 | 30 | 60 |
| Glyceryl trinitrate tablets | 40 | 70 | 100 | — | — |
| Medicinal film of polyacrylamide containing glyceryl trinitrate | 20 | 35 | 60 | 80 | 100 |
| Medicinal film of copolymer of acrylamide, vinylpyrrolidone and ethyl acrylate (1:1:1) containing glyceryl trinitrate | 25 | 40 | 60 | 75 | 100 |

Thus prepared antianginal medicinal films having prolonged action and improved accuracy of dosage, can be stored for periods of time that considerably exceed expiration time of other medicinal forms such as drageé, tablets, granules, etc.

For a better understanding of the invention, the following examples of its practical embodiment are given by way of illustration.

EXAMPLE 1

Antianginal film, having the following composition, in percent by weight, is prepared:
glyceryl trinitrate: 3
polyacrylamide (molecular mass, 970,000): 97

A solution of glyceryl trinitrate in ethyl alcohol, having a concentration of 1 percent by weight, and polyacrylamide solution in water, having a concentration of 10 percent are prepared in glass vessels. Next 970 g of polyacrylamide solution are placed in a vessel provided with a stirrer and 30 g of glyceryl trinitrate solution are added. Stirring is continued for 30 minutes at 80–100 rpm. The solution is then placed in a vacuum cabinet and air is removed from the solution at 10 mm Hg for 2–3 hours at room temperature. The solution is now cast onto a polished metal plate in a 4–5 mm thick layer. The plate is placed in a heated cabinet and kept there for 24 hours at a temperature of 20° C., then for 12 hours at a temperature of 30° C., and finally for 12 hours at 40° C. The obtained medicinal film, 0.5 mm thick, is kept at room temperature for 24 hours, and round discs, 7 mm in diameters, are stamped out mechanically. Each disk contains about 0.5 mg of glyceryl trinitrate.

EXAMPLE 2

Antianginal film containing the following components, in percent by weight, is prepared:
glyceryl trinitrate: 30
copolymer of acrylamide, N-vinylpyrrolidone, and ethylacrylate (1:1:1; mol. weight, 80,000): 70

The components are dissolved in an aqueous-alcohol mixture (75:25) to obtain 10–20 percent solutions. The medicinal film is then prepared by the procedure described in Example 1.

EXAMPLE 3

Antianginal film having the following composition, in percent by weight, is prepared:
glyceryl trinitrate: 10
copolymer of acrylamide, N-vinylpyrrolidone and butyl-acrylate (1:0.5:0.3; mol. weight, 80,000): 90

The components are subsequently dissolved in an aqueous-alcohol mixture (75:25) to obtain 10–20 percent solutions. The further procedure is the same as described in Example 1.

EXAMPLE 4

Antianginal film having the following composition, in percent by weight, is per prepared:
glyceryl trinitrate: 3
copolymer of acrylamide, N-vinylpyrrolidone and ethylacrylate (0.6:0.2:0.2; mol. wt., 50,000); 97 cocoa butter: 3 (with respect to the other components)

The components are subsequently dissolved and dispersed in an aqueous-alcohol mixture (75:25) to obtain 10–20 percent solutions and dispersions of the components. The dispersion is prepared by mechanical stirring. The further procedure is the same as described in Example 1.

EXAMPLE 5

Antianginal film, having the following composition, in percent by weight, is prepared:
glyceryl trinitrate: 5
copolymer of acrylamide, N-vinylpyrrolidone, and ethylacrylate (0.6:0.2:0.2; mol. wt., 500,000): 95
cocoa butter: 30 (with respect to all other components)

The further procedure for preparing the film is the same as described in Example 4.

EXAMPLE 6

Antianginal film, having the following composition, in percent by weight, is prepared:
glyceryl trinitrate: 5
copolymer of acrylamide, N-vinylpyrrolidone, and ethyl acrylate (0.6:0.2:0.2; mol. weight, 500,000): 95
hydrogenized cotton-seed oil: 10 (with respect to all other components)

The method of preparing the film is described in Example 4.

EXAMPLE 7

Antianginal film, having the following composition, in percent by weight, is prepared:
pentaerythritol tetranitrate: 20
copolymer of acrylate, N-vinylpyrrolidone and ethyl acrylate (0.6:0.2:0.2; mol. wt., 500,000): 80
cocoa butter: 10 (with respect to all other components)

The procedure for preparing said medicinal film is the same as described in Example 4.

EXAMPLE 8

Antianginal film, having the following composition, in percent by weight, is prepared:
isosorbide/dinitrate: 20
copolymer of acrylamide, N-vinylpyrrolidone and ethylacrylate (0.6:0.2:0.2; mol. wt., 500,000): 80

The components are subsequently dissolved in an aqueous-alcohol mixture (50:50) to obtain 15–20 percent solutions of the components. The further procedure is the same as described in Example 1.

EXAMPLE 9

Antianginal film having the following coomposition, in percent by weight, is prepared:
pentaerythritol tetranitrate: 20
copolymer of acrylamide, N-vinylpyrrolidone and ethyl acrylamide (0.6:0.2:0.2; mol. wt. 500,000): 80
cocoa butter: 10 (with respect to all other components)

The method is the same as described in Example 4.

EXAMPLE 10

Antianginal film, having the following composition, in percent by weight, is prepared:
glyceryl trinitrate: 5
polyvinylpyrrolidone (mol. wt., 40,000): 95
glyceryl laurate: 10 (with respect to all other components)

The method for preparing the medicinal film is the same as described in Example 4.

EXAMPLE 11

Antianginal film, having the following composition, in percent by weight, is prepared:
glyceryl trinitrate: 5
copolymer of acrylamide, N-vinylpyrrolidone and ethyl acrylate (0.6:0.2:0.2; mol. wt., 500,000): 95
glycerol phthalate: 10 (with respect to all other components)

The method for preparing the medicinal film is the same as described in Example 4.

We claim:

1. In the method of treating ischemic heart disease in patients subject to anginal pectoris by placing anti-anginal coronary vasodilating nitrates buccally for rapid arresting of anginal pectoris attacks, the improvement whereby said buccally placed coronary vasodilating nitrates are highly adhered and remain fixed and glued to a chosen site of the mouth mucosa to insure uniform delivery of said anti-anginal nitrate directly into the blood circulation system through the mouth mucosa, with the great advantage that it is possible to control and easily discontinue the nitrate uptake by removing the unresolved film in cases where it becomes necessary or, on the contrary, to renew the therapy, which comprises placing at a selected site of the mouth mucosa of said patient, an anti-anginal effective amount of said anti-angle nitrate admixed and dissolved in film form with a selected mouth mucosa-soluble, swellable and resolvable polymeric film-forming carrier, in which solutions of the biologically resolvable soluble polymer carrier and the active substance were mixed, and a film cast and dried until the residual amount of the solvent does not exceed about 10 percent by weight;

said resolvable, polymeric film forming carrier having been evaluated to determine its ability to provide immediate, uniform and substained release of a safe but adequate dose of said anti-anginal nitrate, for a particular patient, by:

(i) first applying a film of said soluble and resolvable carrier polymer containing no active anti-anginal ingredient, to a chosen site of the mouth mucosa of the patient in the region of the upper gum above the canine or premolars.

(ii) determining the time of full resolution of the film, and (iii) preparing a film containing that dose of the active principle which should be given to the patient during the time required for full resolution of the film, thereby insuring continuous and optimal therapeutic effect during the entire period of dissolution of the film once the film containing the required amount of the anti-anginal preparation is applied to the chosen site of the mouth mucosa of the patient; said film-forming carrier having the ability to:

(a) form labile complex bonds with said anti-anginal coronary vasodilating nitrate;

(b) remain highly adhered to the mouth mucosa, but can be removed to interrupt or discontinue treatment; and (c) release the active principle of said coronary vasodilator nitrate immediately, and thereafter at such a sustained rate and for a period of time that the pharmacodynamic effects as expressed by the mean data of the repeated individual selected standard physical loads with treadmill in combination with ECG-monitoring (i) are detectable practically instantaneously after affixing to the mouth mucosa, (ii) confirm tha presence of a continous therapeutic concentration of said active principle in the patient's blood during resolution of said carrier, and (iii) confirm a bioavailability of said active principle in an amount substantially greater than that obtained with a sublingual nitroglycerin tablet as the standard.

2. The method of claim 1 wherein said polymeric film-forming carrier is selected from the group consisting of homopolymers of acrylamide and vinylpyrrolidone and their copolymers with acrylates.

3. The method of claim 2 wherein said polymeric carrier is a homopolymer of acrylamide.

4. The method of claim 2 wherein said polymeric carrier is a homopolymer of vinyl pyrrolidone.

5. The method of claim 2 wherein the polymeric carrier is a copolymer of acrylamide.

6. The method of claim 2 wherein the polymeric carrier is a copolymer of vinyl pyrrolidone.

7. The method of claim 2 wherein the polymeric carrier is a copolymer of acrylamide and vinyl pyrrolidone with an acrylate, comprised of about 99 to 70% by weight of acrylamide and vinyl pyrrolidone and about 1 to 30% by weight of acrylate.

8. The method of claim 2 wherein the acrylate has a molecular weight of from about 50,000 to about 1,000,000.

9. The method of claim 1 wherein said anti-anginal nitrate is selected from the group consisting of glycerol trinitrate, pentaerythritol tetranitrate, and isosorbidedinitrate.

10. The method of claim 1 wherein the anti-anginal nitrate is present in an amount of from about 3.0 to about 30 weight percent based on the total weight of said nitrate and carrier.

11. The method of claim 1 wherein from about 3 to about 30% be weight of a dispersed solid fat melting at temperatures of from 30° to 50° C. is present based on the total weight of said nitrate and carrier.

12. The method of claim 11 wherein said solid fat is selected from the group consisting of cocoa butter, hydrogenized cotton seed oil, glycerol laurate, and glycerol phthalate.

13. The method of claim 1 wherein said polymeric film-forming carrier has the ability fo form labile complex bonds with said anti-anginal coronary vasodilating nitrates, said carrier containing said nitrates having been prepared by mixing solvent solutions of said labile complex bond-forming polymer and said anti-anginal nitrate, removing air from the solution in vacuum at room termperature, casting a film and drying the film at temperatures up to 40° C.

* * * * *